(12) United States Patent
Krueger et al.

(10) Patent No.: US 9,283,389 B2
(45) Date of Patent: Mar. 15, 2016

(54) METHOD OF TREATING MOVEMENT DISORDERS OF A LIVING BEING

(75) Inventors: Rejko Krueger, Tuebingen (DE); Daniel Weiss, Stuttgart (DE)

(73) Assignee: Eberhard-Karls-Universität Tübingen Universitätsklinikum, Tuebingen (DE)

( * ) Notice: Subject to any disclaimer, the term of this patent is extended or adjusted under 35 U.S.C. 154(b) by 0 days.

(21) Appl. No.: 13/493,773

(22) Filed: Jun. 11, 2012

(65) Prior Publication Data

US 2013/0331906 A1 Dec. 12, 2013

(51) Int. Cl.
*A61N 1/36* (2006.01)

(52) U.S. Cl.
CPC ........ *A61N 1/36082* (2013.01); *A61N 1/36067* (2013.01); *A61N 1/36167* (2013.01); *A61N 1/36* (2013.01); *A61N 1/3605* (2013.01); *A61N 1/36021* (2013.01); *A61N 1/36071* (2013.01)

(58) Field of Classification Search
CPC ... A61N 1/36; A61N 1/3605; A61N 1/36021; A61N 1/36082; A61N 1/36071; A61N 1/36167; A61N 1/36067
USPC ...................................................... 607/45, 46
See application file for complete search history.

(56) References Cited

U.S. PATENT DOCUMENTS

| | | | |
|---|---|---|---|
| 2002/0177882 A1* | 11/2002 | DiLorenzo | 607/45 |
| 2006/0161219 A1* | 7/2006 | Mock et al. | 607/45 |
| 2006/0212093 A1* | 9/2006 | Pless et al. | 607/45 |
| 2011/0112590 A1* | 5/2011 | Wu et al. | 607/2 |

OTHER PUBLICATIONS

Aziz et al., "The Role of Descending Basal Ganglia Connections to the Brain Stem in Parkinsonian Akinesia," *British J. of Neurosurgery*, 12(3):245-249 (1998).
Breit et al., "Lesion of the Pedunculopontine Nucleus Reverses Hyperactivity of the Subthalamic Nucleus and Substantia Nigra Pars Reticulata in a 6-Hydroxydopamine Rat Model," *European Journal of Neuroscience*, 24:2275-2282 (2006).
Chastan et al., "Effects of Nigral Stimulation on Locomotion and Postural Stability in Patients with Parkinson's Disease," *Brain*, 132:172-184 (2009).
Deuschl et al., "A Randomized Trial of Deep-Brain Stimulation for Parkinson's Disease," *The New England Journal of Medicine*, 355:896-908 (2006).
Ferraye et al., "Effects of Pedunculopontine Nucleus Area Stimulation on Gait Disorders in Parkinson's Disease," *Brain*, 133:205-214 (2010).
Jenkinson et al., "Pedunculopontine Nucleus Electric Stimulation Alleviates Akinesia Independently of Dopaminergic Mechanisms," *NeuroReport*, pp. 1-3 (2006).

(Continued)

*Primary Examiner* — Niketa Patel
*Assistant Examiner* — Lindsey G Hankins
(74) *Attorney, Agent, or Firm* — Marshall, Gerstein & Borun LLP

(57) ABSTRACT

The present invention relates to a method of treating movement disorders of a living being, a method of treating refractory gait disturbances of a human Parkinson's disease patient being affected by gait disturbances, and an apparatus for deep brain stimulation (DBS) of a living being affected by movement disorders.

15 Claims, 4 Drawing Sheets

Kinetra

Strategy 1:
*constant* STN+SNr
130Hz, 3.0V, 60μs

Effective for 2-3 days
then tolerance and
recurrent falls

Activa PC

Strategy 2:

,Daytime'
Group A: 130Hz [STN+SNr]

Solution
Nocturnal
discontinuation of
SNr stimulation

,Nighttime'
Group B: 130Hz [STNmono]

(56) References Cited

OTHER PUBLICATIONS

Kleiner-Fisman et al., "Subthalamic Nucleus Deep Brain Stimulation: Summary and Meta-Analysis of Outcomes," *Movement Disorders*, 21 (Supp. 14):S290-S304 (2006).

Krack et al., "Five-Year Follow-Up of Bilateral Stimulation of the Subthalamic Nucleus in Advanced Parkinson's Disease," *The New England Journal of Medicine*, 349:1925-1934 (2003).

Moore et al., "Freezing of Gait Affects Quality of Life of Peoples with Parkinson's Disease Beyond its Relationships with Mobility and Gait," *Movement Disorders*, 22(15):2192-2195 (2007).

Moreau et al., "STN-DBS Frequency Effects on Freezing of Gait in Advanced Parkinson Disease," *Neurology*, 71:80-84 (2008).

Moro et al., "Unilateral Pedunculopotine Stimulation Improves Falls in Parkinson's Disease," *Brain*, 133:215-224 (2010).

Stefani et al., "Bilateral Deep Brain Stimulation of the Pedunculopontine and Subthalamic Nuclei in Severe Parkinson's Disease," *Brain*, 130:1596-1607 (2007).

Weaver et al., "Bilateral Deep Brain Stimulation vs Best Medical Therapy for Patients with Advanced Parkinson Disease: A Randomized Controlled Trial," *JAMA*, 301(1):63-73 (2009).

Weiss et al., "Combined Stimulation of the Substantia Nigra Pars Reticulata and the Subthalamic Nucleus is Effective in Hypokinetic Gait Disturbance in Parkinson's Disease," *J. Neurol.*, 258:1183-1185 (2011).

Weiss et al., "Combined STN/SNr-DBS for the Treatment of Refractory Gait Disturbances in Parkinson's Disease: Study Protocol for a Randomized Controlled Trial," *Trials*, 12:222-228 (2011).

\* cited by examiner

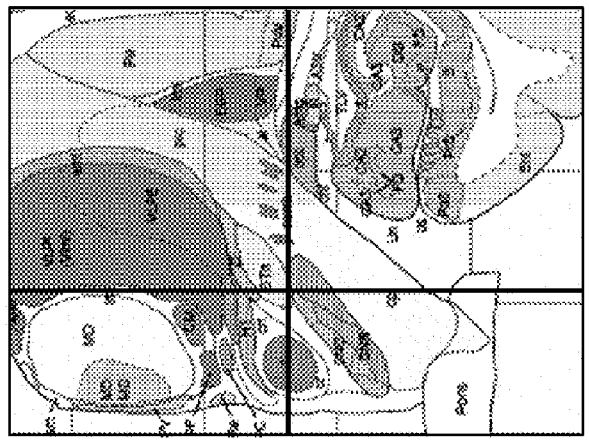
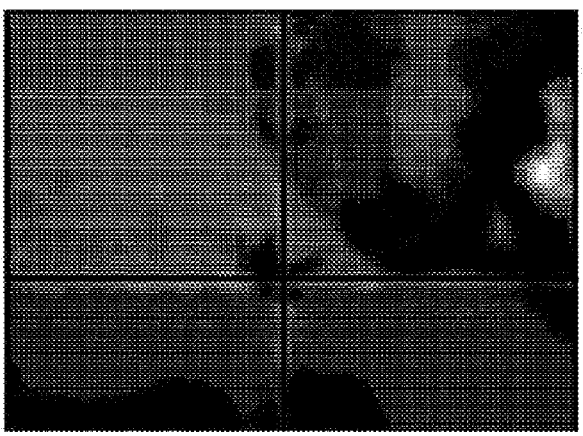
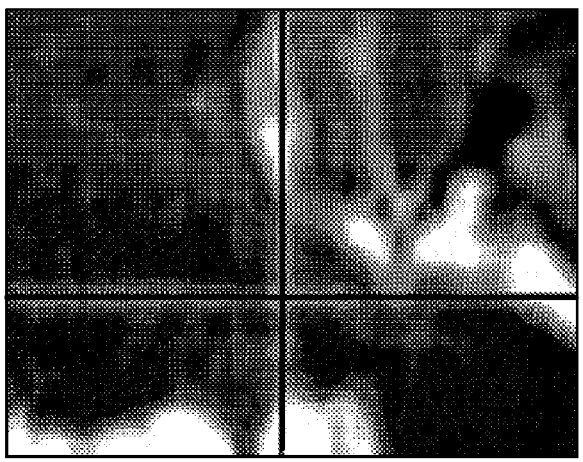
SNr: dorsolateral part bordering caudal STN
9-12 mm lateral [x] (rel. MCP)
2-4 mm posterior [y]
5-8 mm inferior [z]
Fig. 1B

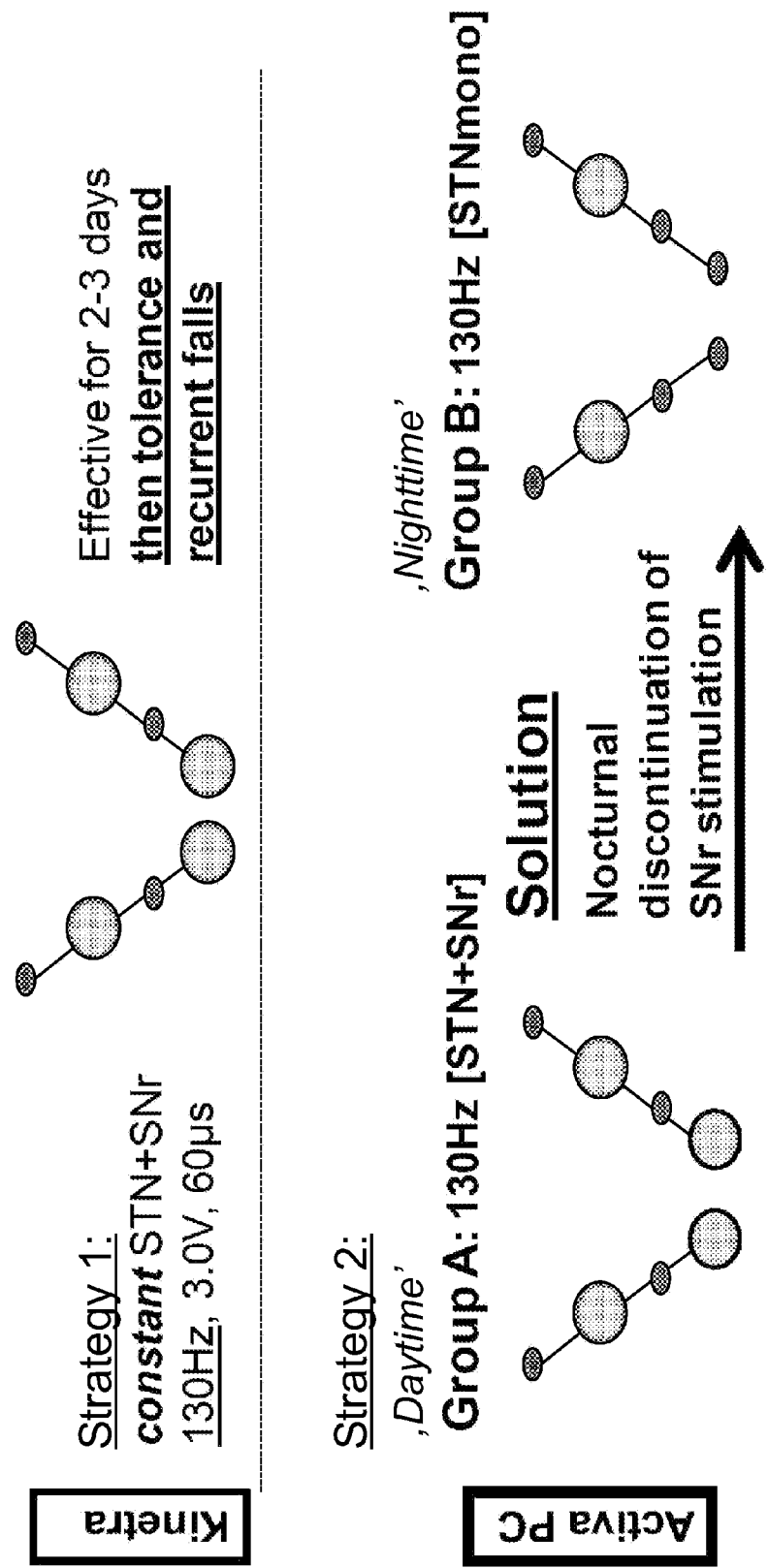

METHOD OF TREATING MOVEMENT DISORDERS OF A LIVING BEING

BACKGROUND OF THE INVENTION

1. Field of the Invention

The present invention relates to a method of treating movement disorders of a living being, a method of treating refractory gait disturbances of a human Parkinson's disease patient being affected by gait disturbances, and an apparatus for deep brain stimulation (DBS) of a living being affected by movement disorders.

2. Related Prior Art

Movement disorders refer to a group of diseases and syndromes affecting the ability to produce and control movement. Examples include akathisia (inability to sit still), akinesia (lack of movement), ataxia (gross lack of coordination of muscle movements), bradykinesia (slow movement), tremor, spasms, gait disturbances etc.

Parkinson's disease (PD) is the most common neurogenerative movement disorder. Severe gait disturbances in idiopathic PD are observed in up to 80% of the patients in advanced disease stages with important impact on quality of life.

Therapeutic deep brain stimulation (DBS) of the subthalamic nucleus (STN) as an evidence-based PD therapy generally ameliorates segmental symptoms and motor fluctuations; cf. Deuschl et al.: A randomized trial of deepbrain stimulation for Parkinson's disease. N Engl J Med 2006, 9:896-908; Kleiner-Fisman et al.: Subthalamic nucleus deep brain stimulation: summary and meta-analysis of outcomes. Mov Disord 2006, 21(Suppl 14):290-304; Weaver et al.: Bilateral deep brain stimulation vs. best medical therapy for patients with advanced Parkinson disease: a randomized controlled trial. Jama 2009, 1:63-73.

However, in PD axial symptoms and in particular gait disturbances may respond unfavorably and generally aggravate in parallel with the underlying neurodegeneration; cf. Krack et al.: Five-year follow-up of bilateral stimulation of the subthalamic nucleus in advanced Parkinson's disease. N Engl J Med 2003, 349:1925-1934; Moore et al.: Freezing of gait affects quality of life of peoples with Parkinson's disease beyond its relationships with mobility and gait. Mov Disord 2007, 22:2192-2195; Moreau et al.: STN-DBS frequency effects on freezing of gait in advanced Parkinson disease. Neurology 2008, 71:80-84. In this condition, increasing intensity of high-frequent STN-DBS at 130 Hz even worsens the condition; cf. Moreau et al., loc cit.

Currently, several approaches are under investigation in order to address the therapeutic need for gait disturbances of PD patients refractory to dopaminergic treatment and STN-DBS. STN-DBS on lower frequencies, e.g. at 60 Hz can improve gait disturbances, however is limited by the recurrence of segmental symptoms like tremor, bradykinesia and rigidity; cf. Moreau et al. loc cit.

Stimulation of the pedunculopontine area for refractory gait disturbances remains controversial at the moment Ferraye et al.: Effects of pedunculopontine nucleus area stimulation on gait disorders in Parkinson's disease. Brain 2010, 133:205-214; Moro et al.: Unilateral pedunculopontine stimulation improves falls in Parkinson's disease. Brain 2010, 133:215-224; Stefani et al.: Bilateral deep brain stimulation of the pedunculopontine and subthalamic nuclei in severe Parkinson's disease. Brain 2007, 130:1596-1607.

Several experimental lines of evidence demonstrated the integrative role of reciprocal brainstem circuitries including substantia nigra pars reticulata (SNr) and the pedunculopontine area; Aziz et al.: The role of descending basal ganglia connections to the brain stem in parkinsonian akinesia. Br J Neurosurg 1998, 12:245-249; Breit et al.: Lesion of the pedunculopontine nucleus reverses hyperactivity of the subthalamic nucleus and substantia nigra pars reticulata in a 6-hydroxydopamine rat model. Eur J Neurosci 2006, 24:2275-2282; Jenkinson et al.: Pedunculopontine nucleus stimulation improves akinesia in a Parkinsonian monkey. Neuroreport 2004, 15:2621-2624.

Importantly, activity of the SNr can be modulated after implantation for conventional STN-DBS, as the caudal electrode contacts are generally located in the caudal border zone of STN and SNr; cf. Chastan et al.: Effects of nigral stimulation on locomotion and postural stability in patients with Parkinson's disease. Brain 2009, 132:172-184;

Recently, a concomitant deep brain stimulation of the substantia nigra pars reticulata additional to the subthalamic nucleus for a time period of 3 to 6 weeks has been suggested to treat gait disturbances in PD; cf. Weiss et al.: Combined stimulation of the substantia nigra pars reticulata and the subthalamic nucleus is effective in hypokinetic gait disturbance in Parkinson's disease. J Neurol 2011, 258:1183-1185; Weiss et al.: Combined STN/SNr-DBS for the treatment of refractory gait disturbances in Parkinson's disease: study protocol for a randomized controlled trial. Trials 2011, 12:222. The contents of both of the before-identified documents of Weiss et al. are herewith incorporated by reference.

However, the inventors have realized that PD patients treated with the approach as disclosed by Weiss et al. develop tolerance after several days of treatment and the gait disturbances recur.

Therefore, there is an unmet need for further symptomatic therapeutic strategies, particularly as gait disturbances generally respond unfavorably to dopaminergic medication and conventional deep brain stimulation of the subthalamic nucleus in advanced disease stages.

SUMMARY OF THE INVENTION

Against this background, the object of the present invention is to provide a novel method of treating movement disorders, in particular gait disturbances, of a living being, by which the disadvantages of the known methods are reduced or even avoided. In particular, such a method should be provided which results in positive effects on the movement disorders over a longer time period and will not evoke tolerance in the patient or at least to a lesser extent.

It's another object of the present invention to provide an apparatus on which the novel method can be operated.

According to the invention, one object is achieved by a method of treating movement disorders of a living being, comprising the following steps:

(a) subjecting a living being affected by movement disorders to a first deep brain stimulation (DBS) protocol for a first time period, (b) subjecting said living being to a second DBS protocol for a second time period following said first time period, and (c) optionally repeating steps (a) and (b), wherein said first DBS protocol differs from said second DBS protocol.

According to the invention said deep brain stimulation protocol refers to a DBS regimen determined by treatment parameters, such as the current or voltage (amplitude) of the administered electrical impulse, the time or duration of the electrical impulse (pulse width), the frequency or the number of administered electrical impulses per time unit, and the target area in the brain where the electrical impulse is delivered to, etc.

In the art usually two types of DBS protocols are used, differing on whether voltage or electrical current is controlled. "Constant current" stimulation provides a specific electrical current and will automatically adjust the voltage depending on the impedance, while the current applied by "constant voltage" stimulation will depend on the tissue impedance that may change over time. In the invention various different protocols are applicable where any of such mentioned parameters is variable.

According to the invention, the first DBS protocol differs from the second DBS protocol. This means that at least one of the before-mentioned parameters defining a DBS protocol differs in the first DBS protocol from the second DBS protocol. It goes without saying, that more than one of such parameters can be different. In other words, the DBS regimen applied in step (a) or the first time period is different from the DBS regimen applied in step (b) or the second time period.

The borders of said first and the second time periods are either determined by the simply scheduling specific time periods such as minutes, hours, days etc. or by biomarkers of the living being, such as activity, positioning or waking/sleeping states.

According to the invention, steps (a) and (b) can be repeated according to the needs of the living being. In particular, steps (a) and (b) can be repeated as long as the movement disorders occur. For example, steps (a) and (b) can be repeated over several hours, days, weeks, months, years or even over the whole life period of the living being.

According to the invention, a living being can be any human or animal subject, in particular a human being such as a patient affected by Parkinson's disease (PD).

The object underlying the invention is herewith fully achieved.

The inventors have realized that the tolerance against a particular DBS protocol developed by a living being suffering from movement disorders can be reduced or even prevented if said living being is subjected to a specific DBS protocol only for a limited time period. Following said limited time period a different DBS protocol is to be applied for another limited period of time. According to the invention, the living being suffering from movement disorders is subjected to discontinued deep brain stimulation. By doing so, tolerance is reduced or even avoided and the living being benefits from an enduring improvement of the movement disorders.

According to a further development said first DBS protocol comprises the simultaneous delivery of electrical impulses to two different brain areas of said living being, and said second DBS protocol comprises the delivery of electrical impulses to one brain area of said living being.

The inventors have realized that the development of tolerance is largely avoided if the living being is in the first time period stimulated at two different brain areas and then in the second time period at only one brain area. Preferably, the delivery of the electrical impulses to said two different brain areas in the first time period is affected in an alternating order. Such specific stimulation pattern is referred to as "interleaved pulses" or "interleaving pulses"; cf. Weiss et al. Trials 2011, loc cit.

According to a further development, in said first DBS protocol the first brain area is the subthalamic nucleus (STN) and the second brain area is the substantia nigra pars reticulata (SNr), and preferably in said second DBS protocol said one brain area is the subthalamic nucleus (STNmono).

In contrast to the protocol disclosed in Weiss et al., Trials 2011, loc cit., where a [STN+SNr] stimulation is constantly administered over time period of 3 to 6 weeks, the inventors limit such [STN+SNr] stimulation for a specific time period and immediately after the expiry of the first time period switch to an [STNmono] stimulation for a second time period. After the expiry of the second time period again the [STN+SNr] stimulation can be applied. The [STN+SNr] and [STNmono] simulation alternate or rotate, respectively.

According to a further development said first and said second time periods are determined by the activity states of said living being. For example, said first time period is determined by the waking and/or activity state of the living being, and said second time period is determined by the sleeping and/or resting states of said living being.

According to this embodiment, the living being is subjected to said first DBS protocol during its waking or activity phase, e.g. at daytime, and it is subjected to the second DBS protocol during its sleeping or resting phase, e.g. at nighttime. As the inventors have realized, the alternation of the DBS protocols in such a manner, e.g. as a function of daytime and nighttime activity of the patient, provides particularly good therapeutic results and an enduring amelioration of the movement disorders.

According to a preferred embodiment of the method according to the invention said activity states of said living being are measured by means of a sensor, for example an accelerometer.

This further development has the advantage that a precondition for an automating of the method or the establishment of a so-called "closed-loop" system is realized. The sensor measures and detects the state of activity of the living being and can provide a signal to the DBS apparatus or brain pacemaker, respectively. Depending on the activity state or signal measured by the sensor the appropriate DBS protocol will be initiated.

In a further development, transition from step (a) to step (b) is automatically initiated after the expiry of said first time period or when the activity state of said living being is changed from a first state such as the waking and/or activity state to a second state different from said first state, such as the sleeping and/or resting state, and, optionally, transition from step (b) to step (c), i.e. back to (a) is automatically initiated after the expiry of said second time period or when the activity state of said living being is changed from said second state to said first state.

This embodiment provides for an automating of the method according to the invention. The transition from one step to another can either be determined by a simple timer or a feed-back system involving the sensor that detects the activity states of the living being and delivers a signal to a control unit which, finally, initiates the transition.

According to a further development of the method according to the invention said movement disorders are gait disturbances and, preferably, said living being is a human Parkinson (PD) patient.

This embodiment has the advantage that a particularly problematic kind of movement disorder and a clinical syndrome are treated for which, so far, no satisfying therapeutic approaches exist.

Another object of the invention is an apparatus for deep brain stimulation (DBS) of a living being affected by movement disorders, comprising an electrical pulse generator, at least one electrode connected to the pulse generator, said electrode is adapted to deliver electrical impulses to brain areas of a living being, a control unit configured to control said electrical pulse generator to generate said electrical impulses, wherein the control unit is configured to control said pulse generator in accordance with a first DBS protocol for a first time period, and in accordance with a second DBS protocol for a second time period, and wherein said control unit alternates between said first and second DBS protocols.

Said apparatus is adapted to operate the method according to the invention. Therefore, the features, characteristics and advantages disclosed for the method according to the invention apply to the apparatus of the invention accordingly.

Said apparatus can be a neurostimulator or "brain pacemaker", respectively.

The at least one electrode is preferably adapted to deliver electrical impulses to such brain areas which are functionally and anatomically distinct.

The at least one electrode and the pulse generator can be realized as a common implantable device, which is sometimes only referred to as "implantable pulse generator" (IPG).

In a preferred embodiment the apparatus according to the invention comprises at least two electrodes. Preferably, one electrode is configured to be positioned in a first brain area such as the subthalamic nucleus (STN), and the second electrode is configured to be positioned in the substantia nigra pars reticulata (SNr). This experimental setup allows a simultaneous or alternating delivery of electrical impulses to two different brain areas, including the delivery of "interleaved pulses", and the use of [STN+SNr] and [STNmono] simulation.

According to a further development the apparatus according to the invention further comprises a sensor, such as an accelerometer, configured to detect the activity states of said living being.

This further development establishes the pre-conditions for a so-called "closed-loop" system. The sensor detects the activity state of said living being and provides a corresponding signal to the control unit. In case the living being is in a first activity state, such as the waking state, the control unit controls the pulse generator in accordance with the first DBS protocol. When the activity state of said living being is changed from said first to a second activity state, such as the sleeping and/or resting state, the control unit controls the pulse generator in accordance with the second DBS protocol. Such feedback system can be operated in an automated manner and, thereby, creates a "closed-loop" system.

It will be understood that the features of the invention mentioned above and those yet to be explained below can be used not only in the respective combination indicated, but also in other combinations or in isolation, without leaving the scope of the present invention.

Exemplary embodiments of the invention are explained in more detail in the following description and are represented in the drawings.

Figure 3:
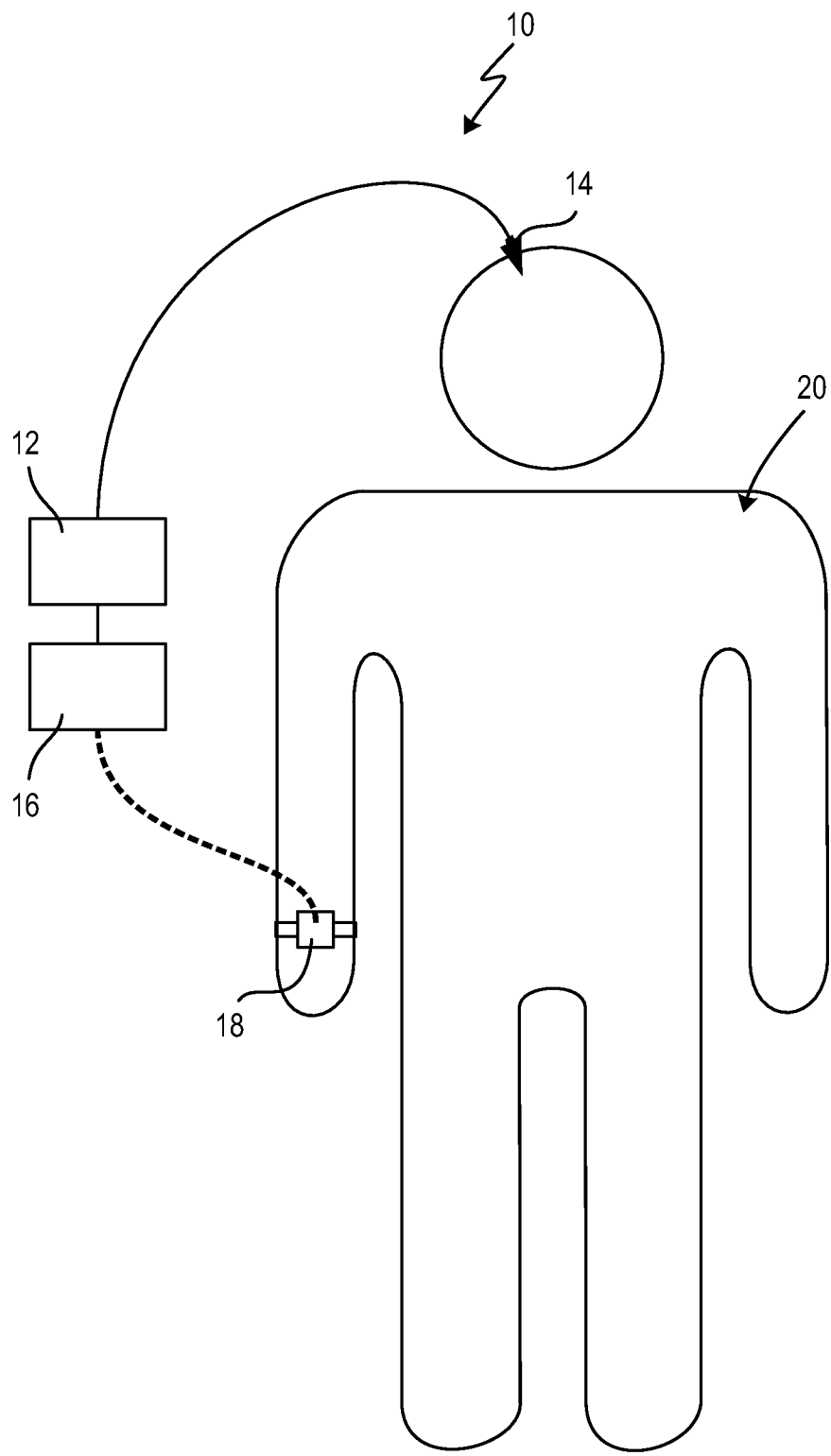

(B) shows the anatomical localization of the subthalamic nucleus (STN) and in the substantia nigra pars reticulata (SNr);

FIG. 2 schematically illustrates conventional constant [STN+SNr] deep brain stimulation of a PD patient at 130 Hz, 3.0 V, 60 μs, resulting in the development of tolerance (top), and alternating [STN+SNr] deep brain stimulation at daytime (Group A) and [STNmono] deep brain stimulation at nighttime (Group B);

FIG. 3 schematically illustrates the design of the apparatus for deep brain stimulation as developed by the inventors.

DESCRIPTION OF PREFERRED EMBODIMENTS

Study Design

Patients with idiopathic Parkinson's disease and refractory gait disturbances under best individual subthalamic nucleus stimulation and dopaminergic medication are enrolled into an ongoing double-blind 2×2 crossover clinical trial. This trial consists of two arms. Severity of the gait disturbance are assessed after 30 min ('short term') and a three week follow-up ('long term') of both (i) conventional stimulation of the STN area [STNmono] and (ii) combined stimulation of the STN area and the caudal STN/SNr border zone [STN+SNr]. Up to date 11 out of planned 12 consecutive patients were randomised on blocks to the two treatment conditions in a 1:1 ratio and treatments will be crossed-over after three weeks of follow-up, respectively. Moreover, a baseline assessment 'off dopaminergic medication' is performed in order to assess short-term effects and to assure optimal stimulation parameters of the conventional STN-DBS [STNmono]. A composite 'axial score' including the major clinical and anamnestic items on gait, posture and balance function from UPDRSII (items 13-15) and UPDRS III (items 27-31) constitutes the primary outcome measure.

Inclusion Criteria
  Written informed consent
  Age: between 18 and 80 years
  Idiopathic Parkinson's disease (according to the "British Brain Bank criteria" including genetic forms and therapy with STN-DBS (ACTIVA pulse generator)
  Optimized subthalamic stimulation (refer 'treatment' section)
  Gait disturbance refractory to best individual STNDBS (STNmono) and dopaminergic therapy: composite 'axial score' in the best clinical [MedOn/STNmono] condition≥12
  Clinical and image-guided or electrophysiological confirmation of (i) at least one of the two rostral contacts of the quadripolar electrode localized in the STN area.
  Dopaminergic medication constant for at least four weeks prior to study enrolment
  Implantation of the DBS electrodes at least 6 months before study enrolment
  Disease duration 5 years Exclusion Criteria
  Cognitive impairment (Mini Mental State Exam <25)
  Participation in other clinical trials within the past three months and during enrolment in our study
  Suicidality, Psychosis
  Other severe pathological chronic condition that might confound treatment effects or interpretation of the data
  Pregnancy
  Acute adverse effects from stimulation on contacts in the caudal STN/SNr border zone Outcome Measures The primary outcome measure is defined as the difference of the composite 'axial score' including the major UPDRS II and III items of gait, balance and posture after 30 min ('short term') or three weeks ('long term') of double-blind treatment with either (i) conventional [STNmono] or (ii) combined [STN+SNr-DBS]. The secondary efficacy variables enable a differentiated assessment of specified axial symptoms, namely freezing of gait (including provoking maneuvers), gait velocity, clinical balance testing, neuropsychiatric symptoms, and non-motor symptoms.

Study Protocol

Clinical testings at baseline were performed after overnight withdrawal of dopaminergic medication and after optimization of subthalamic stimulation. Follow-up examinations were performed in the 'dopaminergic on state'. Of note, no follow-up examinations with a single active SNr contact were conducted as this previously failed to control for segmental symptoms like tremor, bradykinesia and rigidity. The treatment effects of [STNmono] and [STN+SNr] were assessed after 30 min ('short term') and after three weeks ('long term') of constant stimulation on either setting. In the 'long term' approach the order of the treatment conditions will be randomized and crossed after the first visit.

Sample Size Calculation and Statistical Analysis

Primary Endpoint

The primary endpoint for the statistical evaluation of the therapy is the change in composite 'axial score'. The 'axial score' is built by 8 items from the UPDRS II and III, all 5-point rated. For the statistical evaluation the five rating points are represented by the numbers 0 to 4, which represent increasing levels of pathology. The 'axial score' will be scored by the sum of the ratings across the 8 items (range 0 to 32). As change in UPDRS scores is a common primary efficacy outcome measure in Parkinson's disease and only items of the original UPDRS are required for the definition of the primary endpoint the statistical evaluation methods should be based on the psychometric validation of the UPDRS and no own validation studies are necessary. The primary endpoint for the statistical evaluation will be the change in 'axial score' from baseline to visit 2 (after 6 weeks). For every patient two change-scores for the two phases in the Cross-Over were determined. By means of a paired t-test the null hypothesis of equality of the two therapies concerning the change in 'axial score' were tested. The decision for maintaining or rejecting the null hypothesis was made applying a two-sided test with $a=0.05$. The observed effects were described by use of means and effect sizes including the appropriate 95% confidence intervals. The confirmatory statistical evaluation of the efficacy of the [STN+SNr-DBS] in this trial will be restricted to the primary endpoint. Only the rejection of the null hypothesis was interpreted as statistical evidence for the efficacy of [STN+SNr-DBS]. As no comparable study is available at the moment, the inventors defined an improvement of 4 points on the primary outcome measure 'axial score' to be clinically relevant on hypokinetic gait disturbances and assumed a standard deviation of 4.0 (effect size: 1.0). A sample size of 10 will have 80% power to detect a difference in means of 4.0 (e.g. first condition mean: 16.0 and a second condition mean of 12.0), using a paired t-test with a 0.05 two-sided significance level (sample size estimated using NQuery Advisor 7.0). To adjust for a maximum of two dropouts a total of n=12 patients were included in the study.

Secondary Endpoints

As all secondary endpoints are based on validated scores, the inventors assumed that parametric statistical methods can be used for the analysis. The secondary endpoints were compared and statistically assessed for descriptive purposes and not in a confirmatory sense. The aim is explorative data analysis, not hypothesis testing or generation of evidence for efficacy. Because of the explorative character of this part of the analysis, no a priori statistical analysis plan exists. If adequate, changes of scores over time were analysed with paired t-tests or appropriate statistical methods (eg. Repeated Measurements Anova). If a categorization of scores should be adequate (eg. classification in success vs. failure according to score-cut-offs) the inventors used adequate analysis methods for categorical variables (e.g. McNemar Test). In addition, appropriate statistical methods of explorative data analysis including graphical methods and descriptive statistics were used.

Measurement of Gait Disturbances

Berg Balance Scale (BBS): test which evaluates postural stability and balance, by assessing the performance of functional tasks; total score=56, low scores meaning higher imbalance or increase of postural instability.

Freezing of gait questionnaire (FOG-Q): form to assess freezing of gait in daily living; score 0-24, higher score meaning more severe freezing of gait.

Freezing of Gait Assessment Course: Clinical instrument to rate freezing of gait (range from 0 to 36 points, higher score meaning more freezing and gait disorder).

CAPSIT-PD: core assessment program for surgical interventional therapies in Parkinson's disease.

Electrode Localization and Treatment Optimization of subthalamic stimulation is mandatory prior to study enrolment. Based on the current knowledge for optimized DBS programming (i) gait disturbances emerge and progress in the first years after introduction of subthalamic stimulation, (ii) a further increase of the stimulation amplitudes may even aggravate the gait disturbance, and (iii) the stimulation intensity of the lower extremity with longer step length should be reduced compared to the worse affected side—this was previously demonstrated to ameliorate gait symmetry with beneficial effects to gait disturbances, presumably freezing of gait. These actions have been taken before considering combined [STN+SNr] stimulation, however, even if applied a substantial proportion of patients continues to exhibit refractory gait disturbances.

After written informed consent and screening for inclusion criteria, patients have been examined in the baseline condition 'off dopaminergic medications' in order to assure optimization of the best individual stimulation parameters of the conventional STN stimulation [STNmono] and to determine the short-term effects of either stimulation setting.

Figure 1A:
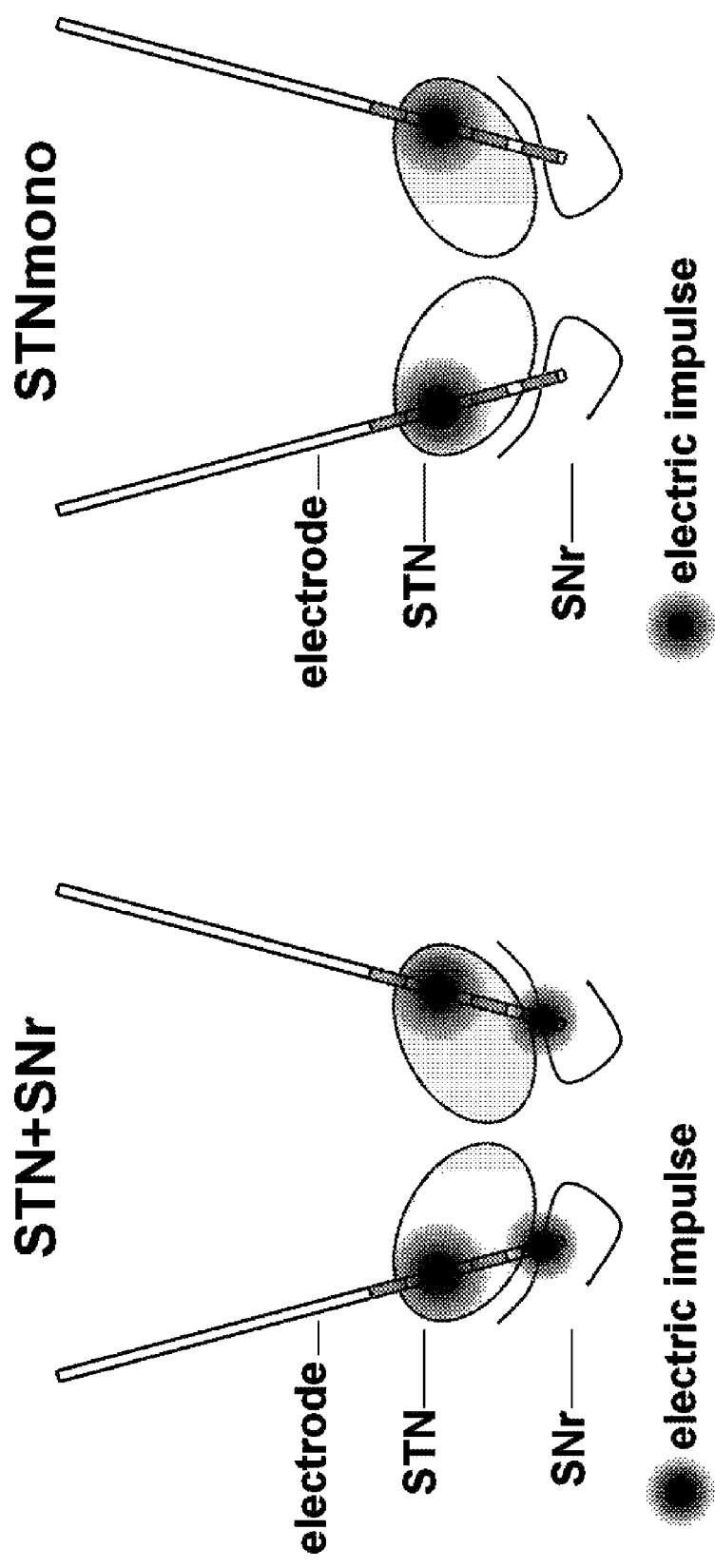
FIG. 1 (A) schematically illustrates the electrode localization in the subthalamic nucleus (STN) and in the substantia nigra pars reticulata (SNr) in the [STN+SNr] deep brain stimulation protocol (left) and in the [STNmono] deep brain stimulation protocol (right)

The localization of the electrodes for both the [STN+SNr] and the [STNmono] treatment is schematically illustrated in FIG. 1A.

To support the assumption that the point of the electrode (the deepest contact) is localized in the caudal border zone of STN and SNr the inventors combined preoperative and postoperative MRI recordings with a reference brain and defined the coordinates of this electrode point to localize the STN and SNr stimulation contacts; cf. FIG. 1B.

The [STN+SNr] condition consisted of the [STNmono] parameters and additional simultaneous stimulation with interleaving pulses on a distal contact with best individual amplitude, 60 μs pulse width, and 125 Hz frequency were introduced depending on individual thresholds for side effects from current spreading. In the baseline examination a randomized clinical evaluation of the treatment conditions [StimOff], [STNmono], and [STN+SNr] in terms of short term effects were performed.

After the baseline examination, patients were randomized to either [STNmono] or [STN+SNr] treatment and scheduled at 30 min ('short term') or three weeks ('long term') of constant stimulation (Visit 1). After this first endpoint assessment 'long term' treatment was crossed-over and patients were re-scheduled after further three weeks of constant stimulation for the second endpoint assessment (Visit 2). The follow-up period in the 'long term' treatment is—due to the current clinical evidence—sufficiently long to control adequately for carry-over effects since the endpoint assessment in the follow-up period were scheduled only after three weeks of constant stimulation on either setting. STN-DBS in PD generally evokes clinical effects within short time intervals ranging from several seconds to few hours and presents completely reversible in the same time range.

Results

Preliminary observations in three Parkinson patients (PD3, PD4, PD6) after a three-week follow-up are demonstrated in the following Table 1:

TABLE 1

Symptoms of PD patients after three weeks of [STN + SNr] deep brain stimulation.

| Predominant symptoms | PD3 [STN + SNr] [STNmono] small steps, freezing | | PD4 [STN + SNr] [STNmono] freezing | | PD6 [STN + SNr] [STNmono] imbalance | |
|---|---|---|---|---|---|---|
| CAPSIT-PD [steps] | 28.5 | 115 | 13.5 | 16 | 11.5 | 12.5 |
| CAPSIT-PD [time] | 13.5 | 71 | 7.5 | 7.5 | 6 | 7, 5 |
| CAPSIT-PD [freezing] | 0 | 1,5 | 0 | 1 | 0 | 0 |
| FOG-Q | 12 | 19 | 12 | 14 | 16 | 15 |
| BBS | 51 | 38 | 55 | 54 | 45 | 51 |
| FOG-AC | 5 | 25 | 6 | 12 | 0 | 1 |

Note that PD3 and PD4 had predominant freezing phenomena and hypokinetic gait disturbance, whereas PD6 presented with imbalance and falls (low values in the FOG-Q and FOG-AC indicate little gait disturbances and good motor skills of the patient; high values indicate more severe gait disturbances and reduced or deteriorated motor skills of the patient).

Whereas table 1 only present results measured after a three-week follow-up the inventors realized an amelioration of gait disturbances in the patients, in particular with respect to "freezing" and "small steps", when measured directly after 30 min of treatment (data not shown).

Therefore, in a next step the inventors analyzed the effect of the [STN+SNr] protocol and [STNmono] protocol with respect to a 'short term' treatment and a 'long term' treatment. In the 'short term' treatment the symptoms of the patients were measured after 30 min of applying either the [STN+SNr] protocol or the [STNmono] protocol. In the 'long term' treatment the symptoms of the patients were measured after 3 weeks of applying either the [STN+SNr] protocol or the [STNmono] protocol. The results observed for two Parkinson patients (PD7 and PD8) are shown in the following Table 2 and 3:

TABLE 2

Symptoms of PD patients after 30 min of [STNmono] and after 30 min of [STN + SNr] deep brain stimulation, quantified by secondary endpoints.

| | Baseline [StimOff] | [STNmono] | [STN + SNr] |
|---|---|---|---|
| PD7 | 33 | 24 | 4 |
| PD8 | 21 | 17 | 7 |

The inventors realized that the motor skills of the patients have been ameliorated in the 'short term' treatment when applying the [STN+SNr] protocol.

TABLE 3

Symptoms of PD patients after 3 weeks of [STNmono] and after 3 weeks of [STN + SNr] deep brain stimulation, quantified by secondary endpoints.

| | Follow-up [STNmono] | [STN + SNr] |
|---|---|---|
| PD7 | 36 | 35 |
| PD8 | 23 | 17 |

The inventors realized that the amelioration which can be observed after a 30 min of [STN+SNr] deep brain stimulation disappeared after a treatment period of 3 weeks, i.e. tolerance develops.

In the following a 70 year old patient with idiopathic Parkinson's disease suffering since two years for severe repetitive falls (up to 10 times daily) and gait disturbance was subjected to the following experiment:

Strategy 1 ("Kinetra"): constant [STN+SNr] deep brain stimulation, 130 Hz, 3.0 V, 60 µs.

Strategy 2 ("Activa PC"): At daytime (Group A) the patient was [STN+SNr] deep brain stimulated with 130 Hz, 3.0 V, 60 µs. At nighttime (Group B) the patient was [STNmono] deep brain stimulated with 130 Hz, 3.0 V, 60 µs. In other words the inventors applied a DBS protocol in the wake or activity state of the patient which has a good effect on gait disturbance and falls, and change in the sleeping or resting state of the patient for a DBS protocol which is ineffective for gait problems and falls but effective for other Parkinsonian motor symptoms.

Both strategies are illustrated in FIG. 2.

Strategy 1 was effective; however the patient developed tolerance within 2 to 3 days with severe falls.

Strategy 2 resulted in large reduction of falls (up to ten times daily before group programming, only three falls in 10 week follow-up after introduction of Groups A and B).

The inventors made similar observations with at least two further patients with substantial short term effect on combined STN+SNr stimulation, but subsequent tolerance during the three-week follow-up.

Apparatus Design

In FIG. 3 the design of the apparatus for deep brain stimulation (DBS) as developed by the inventors is schematically illustrated.

The apparatus 10 comprises an electrical pulse generator 10 which generates electrical impulses, at least one electrode 14 connected to the electrical pulse generator 10, a control unit connected to the electrical pulse generator 10, which control unit 16 is configured to control said electrical pulse generator 12 in accordance with several DBS protocols.

The least one electrode 14 is adapted to deliver electrical impulses to brain areas of a living being 20.

The apparatus further comprises a sensor 18 configured to detect activity states of the living being 20, such as an accelerometer, being fixed to the wrist of the living being 20.

Closed-loop: The sensor 18 detects the activity state of the living being. When the living being is in a waking or activity state the sensor 18 delivers a first signal to the control unit 16. The control unit 16 then runs a first DBS protocol and controls the electrical pulse generator 12 in accordance with said first DBS protocol. The least one electrode 14 then delivers electrical impulses to brain areas of a living being 20 in accordance with said first DBS protocol, e.g. simultaneously to the subthalamic nucleus (STN) and to the substantia nigra pars reticulata (SNr) in an alternating order (interleaved pulses) ([STN+SNr] deep brain stimulation). When the living being is in a sleeping or resting state the sensor 18 delivers a second signal to the control unit 16 which is different from the first signal. The control unit 18 then runs a second DBS protocol and controls the electrical pulse generator 12 in accordance with said second DBS protocol. The least one electrode 14 then delivers electrical impulses to brain areas of a living being 20 in accordance with said second DBS protocol, e.g. to the subthalamic nucleus (STN) only ([STNmono] deep brain stimulation).

What is claimed, is:

1. Method of treating movement disorders of a living being, comprising the following steps:
   (a) subjecting a living being affected by movement disorders to a first deep brain stimulation (DBS) protocol for a first time period,
   (b) subjecting said living being to a second DBS protocol for a second time period following said first time period, and
   (c) repeating steps (a) and (b), wherein said first DBS protocol differs from said second DBS protocol, said first DBS protocol comprises the simultaneous delivery of electrical impulses to two different brain areas of said living being, wherein said first brain area is the subthalamic nucleus (STN) and said second brain area is the substantia nigra pars reticulate (SNr), and said second DBS protocol comprises the delivery of electrical impulses to one brain area of said living being, wherein said one brain area is the subthalamic nucleus (STN);
   wherein said first and said second time periods are determined by the activity states of said living being, said first time period is determined by the waking state, or activity state, or waking and activity states of said living being, and said second time period is determined by the sleeping state, or resting state, or sleeping and resting states of said living being.

2. Method of claim 1, wherein in said first DBS protocol said simultaneous delivery of electrical impulses to said two different brain areas is effected in an alternating order (interleaved pulses).

3. Method of claim 1, wherein said activity states of said living being are measured by means of a sensor.

4. Method of claim 3, wherein said sensor is an accelerometer.

5. Method of claim 3, wherein transition from step (a) to step (b) is automatically initiated when the activity state of said living being is changed from a first state to a second state different from said first state.

6. Method of claim 5, wherein said first state is the waking state, or activity state, or waking and activity states and the second state is the sleeping state, or resting state, or sleeping and resting states.

7. The method of claim 5, wherein transition from step (b) to step (c) is automatically initiated when the activity state of said living being is changed from said second state to said first state.

8. Method of claim 1, wherein transition from step (a) to step (b) is automatically initiated after the expiry of said first time period.

9. The method of claim 8 wherein transition from step (b) to step (c) is automatically initiated after the expiry of said second time period.

10. Method of claim 1, wherein said movement disorders are gait disturbances.

11. Method of claim 1, wherein said living being is a human Parkinson (PD) patient.

12. Method of treating refractory gait disturbances of a human Parkinson patient being affected by gait disturbances, comprising the following steps:
   (a) subjecting said patient for a first time period determined by the waking or activity period of said patient to a first deep brain stimulation (DBS) protocol comprising the simultaneous delivery of electrical impulses to the subthalamic nucleus (STN) and to the substantia nigra pars reticulate (SNr) in an alternating order (interleaved pulses),
   (b) subjecting said patient for a second time period determined by the sleeping or resting period of said patient, ending the first DBS protocol and subjecting said patient to a second DBS protocol comprising the delivery of electrical impulses to the subthalamic nucleus (STN), and
   (c) repeating steps (a) and (b).

13. Apparatus for deep brain stimulation (DBS) of a living being affected by movement disorders, comprising:
   an electrical pulse generator
   at least one electrode connected to the pulse generator, said electrode is adapted to simultaneously deliver electrical impulses to two different brain areas of a living being, and
   a control unit configured to control said electrical pulse generator to generate said electrical impulses,
   wherein the control unit is configured to control said pulse generator in accordance with a first DBS protocol for a first time period, and in accordance with a second DBS protocol for a second time period upon ending the first DBS protocol,
   wherein said control unit alternates between said first and second DBS protocols, said first DBS protocol differs from said second DBS protocol, said first DBS protocol comprises the simultaneous delivery of electrical impulses to two different brain areas of said living being, wherein said first brain area is the subthalamic nucleus (STN) and said second brain area is the substantia nigra pars reticulate (SNr), and said second DBS protocol comprises the delivery of electrical impulses to one brain area of said living being, wherein said one brain area is the subthalamic nucleus (STN), and
   wherein said control unit alternates between said first and second DBS protocols when the activity state of said living being is changed from a first state to a second state, said first state comprising the waking state, or activity state, or waking and activity states and said second state comprising the sleeping state, or resting state, or sleeping and resting states.

14. Apparatus of claim 13, further comprising a sensor configured to detect the activity states of said living being.

15. Apparatus of claim 14, wherein the sensor is an accelerometer.

* * * * *